United States Patent
Rich et al.

(10) Patent No.: US 6,926,670 B2
(45) Date of Patent: Aug. 9, 2005

(54) WIRELESS MEMS CAPACITIVE SENSOR FOR PHYSIOLOGIC PARAMETER MEASUREMENT

(75) Inventors: Collin A. Rich, Ypsilanti, MI (US); Yafan Zhang, Plymouth, MI (US); Nader Najafi, Ann Arbor, MI (US); Matthew Z. Straayer, Ann Arbor, MI (US); Sonbol Massoud-Ansari, Ann Arbor, MI (US)

(73) Assignee: Integrated Sensing Systems, Inc., Ypsilanti, MI (US)

( * ) Notice: Subject to any disclaimer, the term of this patent is extended or adjusted under 35 U.S.C. 154(b) by 392 days.

(21) Appl. No.: 10/054,330

(22) Filed: Jan. 22, 2002

(65) Prior Publication Data

US 2002/0151816 A1 Oct. 17, 2002

Related U.S. Application Data

(60) Provisional application No. 60/263,327, filed on Jan. 22, 2001, and provisional application No. 60/278,634, filed on Mar. 26, 2001.

(51) Int. Cl.[7] .............................................. A61B 8/14
(52) U.S. Cl. ........................................................ 600/459
(58) Field of Search ............................... 600/437–472; 73/625–633; 367/7, 11, 130, 138; 607/36–38, 1, 2, 60; 128/916

(56) References Cited

U.S. PATENT DOCUMENTS 5,337,747 A    8/1994  Neftel
6,101,371 A  *  8/2000  Barber et al. .................. 455/73
6,201,980 B1    3/2001  Darrow et al.
6,268,161 B1    7/2001  Han et al.
6,328,699 B1   12/2001  Eigler et al.
6,567,703 B1  *  5/2003  Thompson et al. ........... 607/60

FOREIGN PATENT DOCUMENTS

EP         0812016       12/1997
WO         WO00/19888     4/2000
WO         WO00/30534     6/2000

OTHER PUBLICATIONS

A Passive Wireless Integrated Humidity Sensor, Timothy Harpster et al. 2001, pp. 553–557.
Electrodeposited Copper Inductors for Intraocular pressure Telemetry; R. Puers et al.; 2001 pp. 124–129.
Hermetically Sealed Inductor–Capacitor (LC) Resonator for Remote Pressure Monitoring; Eun–Chul Park et al.; Sep. 8, 1998; pp. 7124–7128.
Micromachined Planar Inductors on Silicon Wafers for MEMS Applications; Chong H. Ahn et al.

* cited by examiner

Primary Examiner—Ali Imam
(74) Attorney, Agent, or Firm—Brinks Hofer Gilson & Lione

(57) ABSTRACT

The present invention relates to an implantable microfabricated sensor device and system for measuring a physiologic parameter of interest within a patient. The implantable device is micro electromechanical system (MEMS) device and includes a substrate having an integrated inductor and at least one sensor formed thereon. A plurality of conductive paths electrically connect the integrated inductor with the sensor. Cooperatively, the integrated inductor, sensor and conductive paths defining an LC tank resonator.

31 Claims, 9 Drawing Sheets

WIRELESS MEMS CAPACITIVE SENSOR FOR PHYSIOLOGIC PARAMETER MEASUREMENT

CROSS REFERENCE TO RELATED-APPLICATION

This application claims priority to prior U.S. provisional application No. 60/263,327 (filed Jan. 22, 2001) and U.S. provisional application No. 60/278,634 (filed Mar. 26, 2001).

BACKGROUND OF THE INVENTION

Field of the Invention

The present invention generally relates to the field of MEMS (micro-electromechanical systems) sensors and more specifically to a wireless MEMS capacitive sensor for implantation into the body of a patient to measure one or more physiologic parameters.

A number of different biologic parameters are strong candidates for continuous monitoring. These parameters include, but are not limited to blood pressure, blood flow, intracranial pressure, intraocular pressure, glucose levels, etc. Wired sensors, if used have certain inherent limitations because of the passage of wires (or other communication "tethers") through the cutaneous layer. Some limitations include the risks of physical injury and infection to the patient. Another risk is damage to the device if the wires (the communication link) experience excessive pulling forces and separate from the device itself. Wireless sensors are therefore highly desirable for biologic applications.

A number of proposed schemes for wireless communication rely on magnetic coupling between an inductor coil associated with the implanted device and a separate, external "readout" coil. For example, one method of wireless communication (well-known to those knowledgeable in the art) is that of the LC (inductor-capacitor) tank resonator. In such a device, a series-parallel connection of a capacitor and inductor has a specific resonant frequency, expressed as $1/\sqrt{LC}$, which can be detected from the impedance of the circuit. If one element of the inductor-capacitor pair varies with some physical parameter (e.g. pressure), while the other element remains at a known value, the physical parameter may be determined from the resonant frequency. For example, if the capacitance corresponds to a capacitive pressure sensor, the capacitance may be back-calculated from the resonant frequency and the sensed pressure may then be deduced from the capacitance by means of a calibrated pressure-capacitance transfer function.

The impedance of an LC tank resonator may be measured directly or it may also be determined indirectly from the impedance of a separate readout coil that is magnetically coupled to the internal coil. The latter case is most useful for biologic applications since the sensing device may be subcutaneously implanted, while the readout coil may be located external to the patient, but in a location that allows magnetic coupling between the implanted sensing device and readout coil. It is possible for the readout coil (or coils) to simultaneously excite the resonator of the implanted device and sense the reflected back impedance. Consequently, this architecture has the substantial advantage of requiring no internal power source, which greatly improves its prospects for long-term implantation (e.g. decades to a human lifetime).

Such devices have been proposed in various forms for many applications. Chubbuck (U.S. Pat. No. 4,026,276), Bullara (U.S. Pat. No. 4,127,110), and Dunphy (U.S. Pat. No. 3,958,558) disclose various devices initially intended for hydrocephalus applications (but also amenable to others) that use LC resonant circuits. The '276, '110, and '558 patents, although feasible, do not take advantage of recent advances in silicon (or similar) microfabrication technologies. Kensey (U.S. Pat. No. 6,015,386) discloses an implantable device for measuring blood pressure in a vessel of the wrist. This device must be "assembled" around the vessel being monitored such that it fully encompasses the vessel, which may not be feasible in many cases. In another application, Frenkel (U.S. Pat. No. 5,005,577) describes an implantable lens for monitoring intraocular pressure. Such a device would be advantageous for monitoring elevated eye pressures (as is usually the case for glaucoma patients); however, the requirement that the eye's crystalline lens be replaced will likely limit the general acceptance of this device.

In addition to the aforementioned applications that specify LC resonant circuits, other applications would also benefit greatly from such wireless sensing. Han, et al. (U.S. Pat. No. 6,268,161) describe a wireless implantable glucose (or other chemical) sensor that employs a pressure sensor as an intermediate transducer (in conjunction with a hydrogel) from the chemical into the electrical domain.

The treatment of cardiovascular diseases such as Chronic Heart Failure (CHF) can be greatly improved through continuous and/or intermittent monitoring of various pressures and/or flows in the heart and associated vasculature. Porat (U.S. Pat. No. 6,277,078), Eigler (U.S. Pat. No. 6,328,699), and Carney (U.S. Pat. No. 5,368,040) each teach different modes of monitoring heart performance using wireless implantable sensors. In every case, however, what is described is a general scheme of monitoring the heart. The existence of a method to construct a sensor with sufficient size, long-term fidelity, stability, telemetry range, and biocompatibility is noticeably absent in each case, being instead simply assumed. Eigler, et al., come closest to describing a specific device structure although they disregard the baseline and sensitivity drift issues that must be addressed in a long-term implant. Applications for wireless sensors located in a stent (e.g., U.S. Pat. No. 6,053,873 by Govari) have also been taught, although little acknowledgement is made of the difficulty in fabricating a pressure sensor with telemetry means sufficiently small to incorporate into a stent.

Closed-loop drug delivery systems, such as that of Feingold (U.S. Pat. No. 4,871,351) have likewise been taught. As with others, Feingold overlooks the difficulty in fabricating sensors that meet the performance requirements needed for long-term implantation.

In nearly all of the aforementioned cases, the disclosed devices require a complex electromechanical assembly with many dissimilar materials, which will result in significant temperature- and aging-induced drift over time. Such assemblies may also be too large for many desirable applications, including intraocular pressure monitoring and/or pediatric applications. Finally, complex assembly processes will make such devices prohibitively expensive to manufacture for widespread use.

As an alternative to conventionally fabricated devices, microfabricated sensors have also been proposed. One such device is taught by Darrow (U.S. Pat. No. 6,201,980). Others are reported in the literature (see, e.g. Park, et al., Jpn. J. Appl. Phys., 37 (1998), pp. 7124–7128; Puers, et al., J. Micromech. Microeng. 10 (2000), pp. 124–129; Harpster et al., Proc. 14$^{th}$ IEEE Int'l. Conf. Microelectromech. Sys. (2001), pp. 553–557).

Past efforts to develop wireless sensors have separately located the sensor and inductor and have been limited to implant-readout separation distances of 1–2 cm at most, rendering them impractical for implantation much deeper than immediately below the cutaneous layer. This eliminates from consideration wireless sensing applications, such as heart ventricle pressure monitoring or intracranial pressure monitoring, that inherently require separation distances in the range of 5–10 cm. In the present state-of-the-art, several factors have contributed to this limitation on the separation distance including 1) signal attenuation due to intervening tissue, 2) suboptimal design for magnetic coupling efficiency; and 3) high internal energy losses in the implanted device.

In view of the above and other limitations on the prior art, it is apparent that there exists a need for an improved wireless MEMS sensor system capable of overcoming the limitations of the prior art and optimized for signal fidelity, transmission distance and manufacturability. It is therefore an object of the present invention is to provide a wireless MEMS sensor system in which the sensing device is adapted for implantation within the body of patient.

A further object of this invention is to provide a wireless MEMS sensor system in which the separation distance between the sensing device and the readout device is greater than 2 cm, thereby allowing for deeper implantation of the sensing device within the body of a patient.

Still another object of the present invention is to provide a wireless MEMS sensor system in which the sensing device utilizes an integrated inductor, an inductor microfabricated with the sensor itself.

It is also an object of this invention to provide a wireless MEMS sensor system in which the sensing device is batteryless.

A further object of the present invention is to provide a wireless MEMS sensor system.

BRIEF SUMMARY OF THE INVENTION

In overcoming the limitations of the prior art and achieving the above objects, the present invention provides for a wireless MEMS sensor for implantation into the body of a patient and which permits implantation at depths greater than 2 cm while still readily allowing for reading of the signals from the implanted portion by an external readout device.

In achieving the above, the present invention provides a MEMS sensor system having an implantable unit and a non-implantable unit. The implantable unit is microfabricated utilizing common microfabricating techniques to provide a monolithic device, a device where all components are located on the same chip. The implanted device includes a substrate on which is formed a capacitive sensor. The fixed electrode of the capacitive sensor may formed on the substrate itself, while the moveable electrode of the capacitive sensor is formed as part of a highly doped silicon layer on top of the substrate. Being highly doped, the silicon layer itself operates as the conductive path for the moveable electrode. A separate conductive path is provided on the substrate for the fixed electrode.

In addition to the capacitive sensor, the implanted sensing device includes an integrally formed inductor. The integral inductor includes a magnetic core having at least one plate and a coil defining a plurality of turns about the core. One end of the coil is coupled to the conductive lead connected with the fixed electrode while the other end of the coil is electrically coupled to the highly doped silicon layer, thereby utilizing the silicon layer as the conductive path to the moveable electrode.

In order to optimize the operation of the inductor and to permit greater implantation depths, a novel construction is additionally provided for the magnetic core. In general, the optimized magnetic core utilizes a pair of plates formed on opposing sides of the substrate and interconnected by a post extending through the substrate. The windings of the coil, in this instance, are provided about the post.

The external readout device of the present system also includes a coil and various suitable associated components, as well known in the field, to enable a determination of the pressure or other physiologic parameter being sensed by the implanted sensing device. The external readout device may similarly be utilized to power the implanted sensing device and as such the implanted sensing device is wireless.

Integrally formed on the implanted device and microfabricated therewith, may be additionally be active circuitry for use in conjunction with capacitive sensor. Locating this circuitry as near as possible to the capacitive sensor minimizes noise and other factors which could lead to a degradation in the received signal and the sensed measured physiologic parameter. As such, the active circuitry may be integrally microfabricated in the highly doped silicon layer mentioned above.

Further object and advantages of the present invention will become apparent to those skilled in the art from a review of the drawings in connection with the following description and dependent claims.

DETAILED DESCRIPTION OF THE PREFERRED EMBODIMENTS

Figure 1:
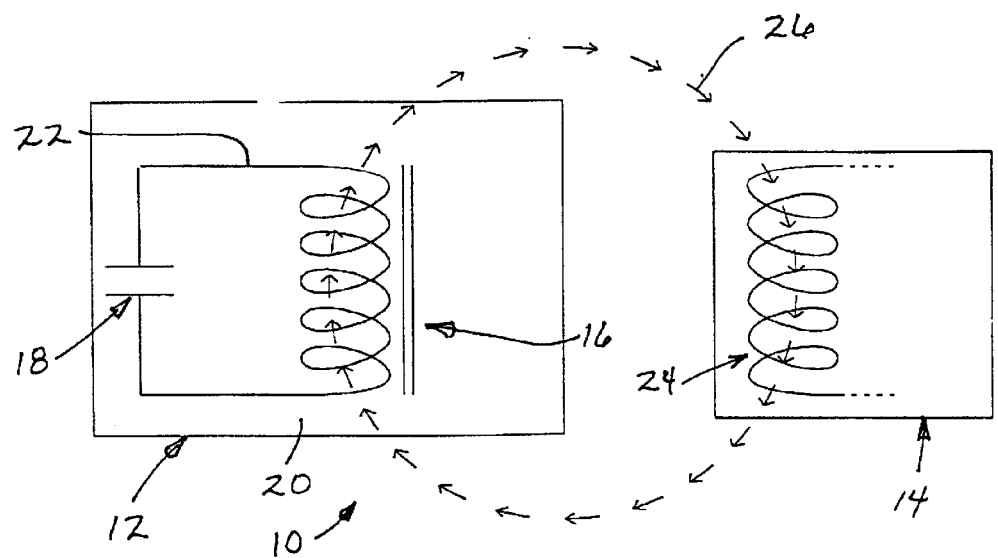
FIG. 1 is a schematic illustration of a wireless MEMS sensor system according the principles of the present invention.

In order to provide for battery-less, wireless physiologic parameter sensing over significant distances greater than 2 cm (e.g. 10 cm), the present invention provides a wireless MEMS sensing system, generally designated at 10 and seen schematically in FIG. 1. The system 10 includes a microfabricated implantable sensing device 12, optimized for coupling with an external readout device 14. The sensing device 12 is provided with an integrated inductor 16 that is conductive to the integration of transducers and/or other components necessary to construct the wireless sensing system 10. As an example, the preferred embodiment integrates a capacitive pressure sensor 18 into a common substrate 20 with the integrated inductor 16. A second inductor 24, in the readout device 14, couples magnetically 26 with the integrated inductor 16 of the sensing device 12.

The readout device 14 is constructed according to techniques well known in the industry and in the sensing field in general. As such, the readout device 14 is not illustrated or described in great detail. It is noted, however, that the readout device 14 may be included, in addition to its inductor 24, signal conditioning, control and analysis circuitry and software, display and other hardware and may be a stand alone unit or may be connected to a personal computer (PC) or other computer controlled device.

Figure 2:
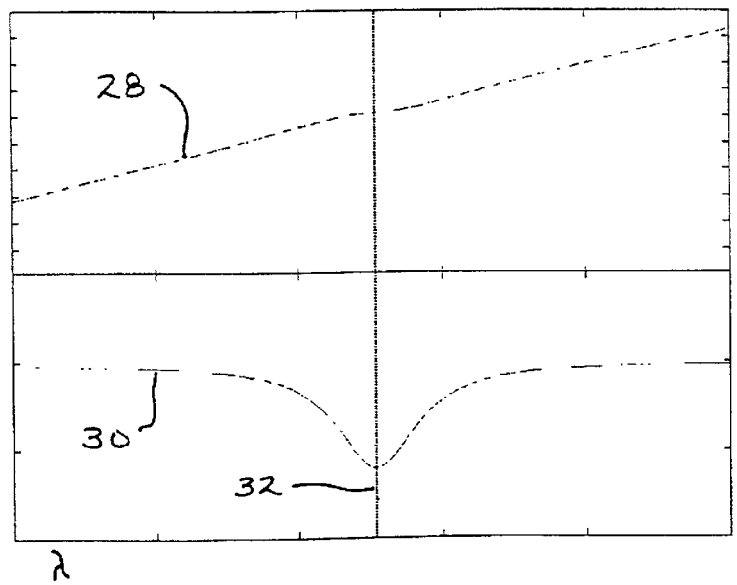
FIG. 2 is a graphical illustration of impedance magnitude and phase angle near resonance, as sensed through a readout coil.

The magnetic coupling 26 seen in FIG. 1 allows the impedance of the LC tank circuit 22 to be sensed by the readout device 14. The typical impedance magnitude 28 and phase angle 30 near resonance 32, as sensed through the readout coil 14, is seen in FIG. 2. Real-time measurement and analysis of this impedance and changes therein allows the sensed pressure to be determined as previously mentioned.

Figure 3:
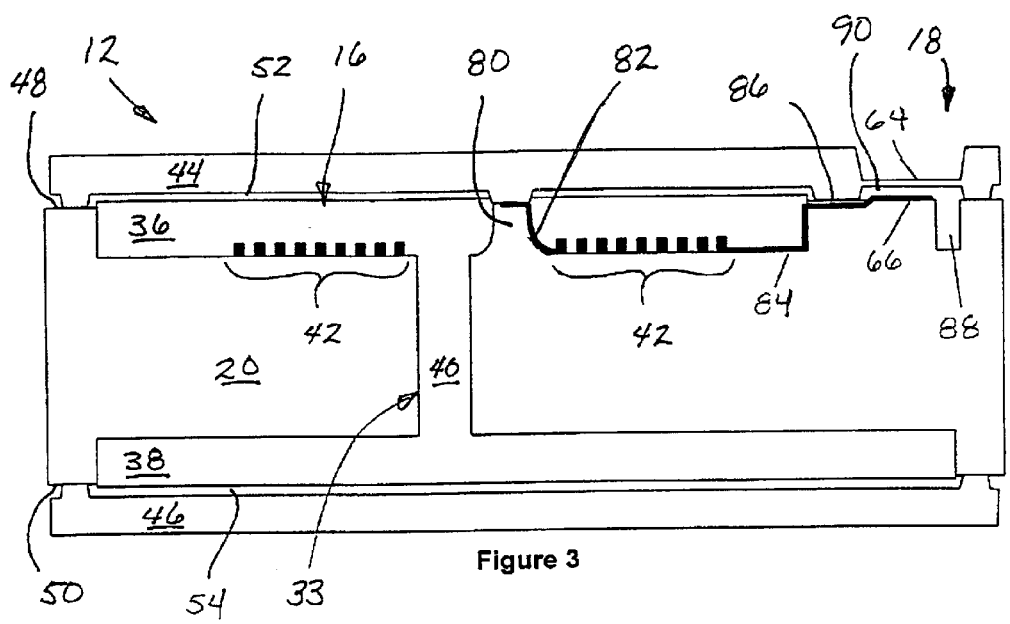
FIG. 3 is a cross-sectional representation of a sensing device embodying the principles of the present invention.

Referring now to FIG. 3, a cross section of a preferred embodiment of the sensing device 12 is illustrated therein. The sensing device 12 includes a main substrate 34 (preferably 7740 Pyrex glass) formed and located within recessed regions of the substrate 34 are those structures forming the integrated inductor 16. The integrated inductor 16 is seen to include a magnetic core 33 defined by a top plate 36, a bottom plate 38 and a post 40 connecting the top plate 36 to the bottom plate 38 and being continuous through the substrate 34. The plates 36 and 38 and the post 40 are preferably constructed of the same material, a ferromagnetic material and are monolithic. The integrated conductor 16 additionally includes a coil 42, preferably composed of copper or other high-conductivity material, successive turns of which surround the post 40 of the magnetic core 33.

In FIG. 3, the coil 42 is seen as being recessed into the top plate 36. The coil 42 may additionally be planar or layered and preferably wraps as tightly as possible about the post 40. If the material of the coil 42 has a high electrical resistance relative to the material of the core 33, (as in a copper coil and NiZn ferrite core system) the core 33, and specifically the top plate 36 may be directly deposited on top of the coil 42 without need for a intermediate insulating layer. If the electrical resistance of the coil material relative to the coil material is not high, an intermediate insulating layer must be included between the successive turns of the coil 42 and the core 33.

Top and bottom cap layers 44 and 46 respectively, are provided over upper and lower faces 48 and 50 of the substrate 20 and over the top and bottom plates 36 and 38 of the magnetic core 33. To accommodate any portions of the magnetic core 33 that extend significantly above or below the upper and lower faces 48 and 50 of the substrate 20, the cap layers 44 and 46 may be provided with recesses 52 and 54, respectively. Preferably, the cap layers 44 and 46 are of monocrystalline silicon. Other preferred materials include polycrystalline silicon, epitaxially deposited silicon, ceramics, glass, plastics, or other materials that can be bonded to lower substrate and/or are suitable for fabrication of the sensor diaphragm. In lieu of a monolithic cap layer, several sub-pieces may be fabricated at separate process steps, together forming a complete cap layer after processing is finished.

Figure 4:
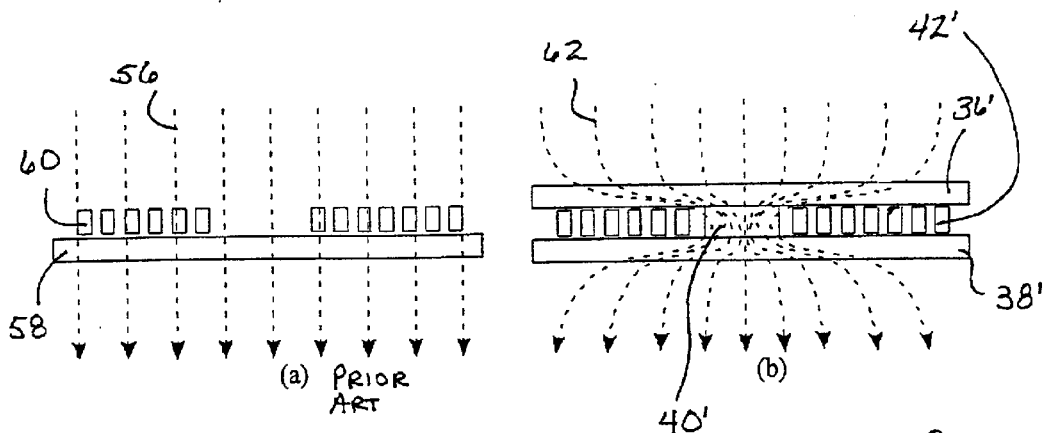
FIGS. 4A and 4B are schematic illustrations of the magnetic field distribution with FIG. 4A illustrating the magnetic field distribution of prior art devices and with FIG. 4B illustrating the magnetic field distribution for a sensing device having a magnetic core embodying the principles of the present invention.

The coupling effectiveness of the integrated inductor 16 is a function of the magnetic flux enclosed by the windings of the coil 42; therefore the coupling is greatest if the structure of the integrated inductor 16 maximizes the flux encompassed by all of the winding loops. FIG. 4A shows schematically the magnetic field distribution 56 in a known inductor structure having a single core layer 58 and associated windings 60. Schematically shown in FIG. 4b is the magnetic field distribution 62 for an inductor structure 16' having upper and lower plates 36' and 38', connected by a post 40' about which windings of a coil 42' are located, as generally seen in the present invention. The design of the present invention optimizes the inductor geometry for maximum field coupling. Placing the plates 36 and 38 on opposite sides of the substrate 20, as in FIG. 3, increases the plate-to-plate spacing. The increased plate spacing creates a localized path of least resistance for the free-space magnetic field of an external readout coil, causing the magnetic field to preferentially pass through the post 40 of the integrated inductor's magnetic core 33. This increases device effectiveness since the coupling efficiency between the sensor and a readout unit increases with the total magnetic flux encompassed by the windings of the inductor. A greater coupling efficiency increases the maximum separation distance between the sensor and a readout unit.

The materials used to form the integrated inductor 16 should be chosen and/or processed to maximize the above mentioned effect and to minimize drift in the inductance value across time, temperature, package stress, and other potentially uncontrolled parameters. A high-permeability material such as NiZn ferrite is used to maximize this effect on the magnetic field and to minimize drift. Other preferred materials include nickel, ferrite, permalloy, or similar ferrite composites.

To the right of the integrated inductor 16 seen in FIG. 3 is the capacitive pressure sensor 18. The capacitive pressure sensor 18 may be constructed in many forms commonly know to those familiar with the art. In the illustrated embodiment, the upper cap layer 44 is formed to define a diaphragm 64. The diaphragm 64 constitutes and may also be referred to as the moveable electrode of the pressure sensor 18. The fixed electrode 66 of the pressure sensor 18 is defined by a conductive layer formed on the upper face 48 of the substrate 20, in a position immediately below the moveable electrode or diaphragm 64. If desired, a conductive layer may additionally be located on the underside of the moveable electrode 64. To prevent shorting between the upper electrode 64 (as defined by either the diaphragm itself or the diaphragm and the conductive layer 68) and the lower electrode 66, one or both of the electrodes 64 and 66 may be provided with a thin dielectric layer (preferably less than 1000 Å) deposited thereon.

Figure 8:
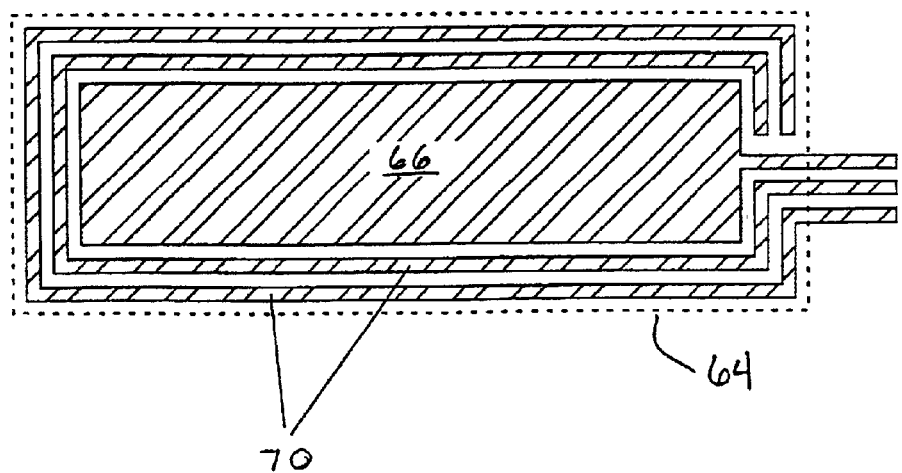
FIG. 8 is a top plane view of a second embodiment of the main electrode in the capacitive sensor portion of the implanted sensing device according to the principles of the present invention.

To improve performance of the capacitive pressure sensor 18, as seen in FIG. 8, one or more secondary electrodes designated at 70 may be located about the fixed electrode 66 near the projected edge of the diaphragm 64 where pressure induced deflection of the diaphragm 64 is minimal. The secondary electrodes 70 experience all of the capacitance-effecting phenomena seen by the main electrode 66, with the exception of any pressure-induced phenomena. The secondary electrodes 70, as such, operate as reference electrodes and by subtracting the secondary electrodes' capacitive measurement from the capacitive measurement of the main electrode 66, most or all non-pressure-induced capacitance changes (signal drift) may be filtered out. Examples as sources of signal drift, that may be filtered out by this method, include thermally induced physical changes and parasitics resulting from an environment with changing dielectric constant, such as insertion of the sensor into tissue. In a preferred embodiment, the secondary (or reference) electrodes 70 would require an additional coil, similar to construction of the previously mentioned coil 42 to form a separate LC tank circuit. It is noted, that both coils may, however, share the same core post 40.

Under normal operation, pressure applied to the exterior or top surface of the capacitive pressure sensor 18 causes the diaphragm 64 (or at least the center portions thereof) to deflect downward toward the fixed electrode 66. Because of the change in distance between the fixed electrode 66 and the moveable electrode 64, a corresponding change will occur in the capacitance between the two electrodes. The applied pressure is therefore translated into a capacitance. With this in mind, it is seen that the capacitance pressure sensor 18 may be operated in either of two modes.

Figure 5:
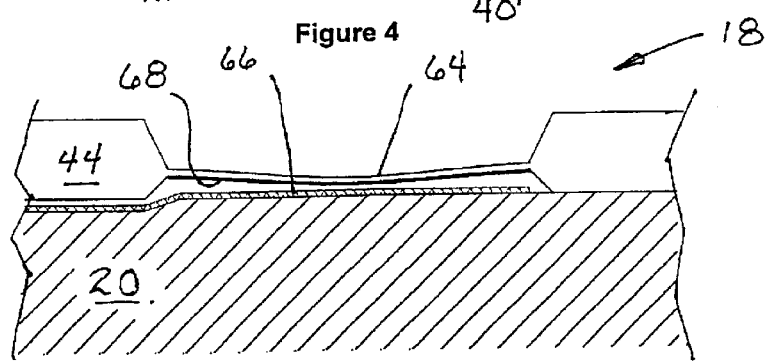
FIG. 5 is an enlarged cross-sectional view of the diaphragm portion of FIG. 3 operating in what is herein referred to as a "proximity" mode.

A first mode, hereinafter referred to as the "proximity" mode, is generally seen in FIG. 5. In this mode of operation, the starting gap between the fixed electrode 66 and the moveable electrode 64, as well as the material and physical parameters for the diaphragm 64 itself, are chosen such that the fixed electrode 66 and the moveable electrode 64will be spaced apart from one another over the entire operating pressure range of the sensor 18. For the standard equation of parallel plate capacitance, $C=\in A/d$, the plate separation d will vary with the applied pressure, while the plate area A and the permittivity $\in$ remain constant.

Figure 6:
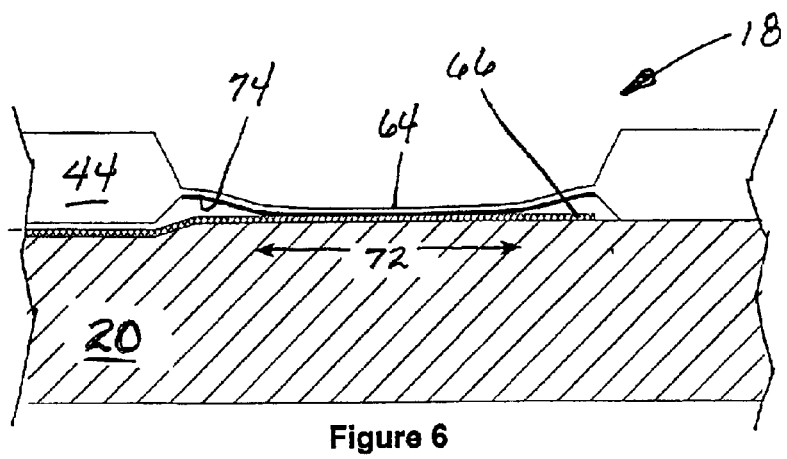
FIG. 6 is a cross-sectional view similar to that seen in FIG. 5 illustrating, however, the diaphragm operating in what is herein referred to as a "touch" mode.

In the touch mode of operation, generally seen in FIG. 6, the geometry (e.g., initial gap spacing between the fixed electrode 66 and the moveable electrode 64) as well as the material and physical parameters of the diaphragm 64 itself, are chosen such that the fixed electrode 66 and the moveable electrode 64 will progressively touch each other over the operating pressure range of the sensor 18. Accordingly, the area 72 of the fixed electrode 66 and the moveable electrode 64 in contact with each other will vary with the applied pressure. In the touch mode of operation, the dominant capacitance is the capacitance of the regions of the fixed electrode 66 and the moveable electrode 64 in contact with one another (if the dielectric coating 74 is thin compared to the total gap thickness, thereby yielding a relatively small effective plate separation distance d). In the capacitance equation mentioned above, plate separation d and permittivity $\in$ will remain constant (at approximately that of the dielectric thickness) while the plate contact area A varies with the applied pressure.

Figure 7:
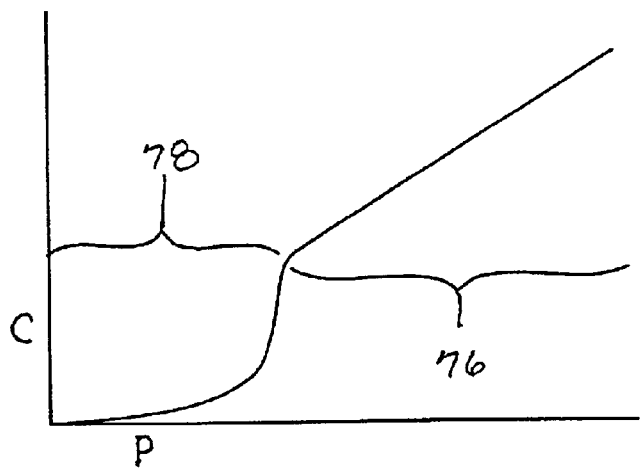
FIG. 7 is a capacitance versus pressure curve in the proximity and touch modes of operation.

In the graph of FIG. 7, capacitance-pressure relationship in the proximity and touch modes, respectively designated at 76 and 78, are seen. From a practical standpoint, the operational mode may be chosen based upon sensitivity, linearity, and dynamic range requirements. The touch mode typically yields higher sensitivity with a more linear output, but involves mechanical contact between surfaces and therefore requires a careful choice of the materials to avoid wear induced changes in performance of the pressure sensor 18.

To permit the innermost turn of the coil 42 to be electrically connected to the moveable electrode 66, a post 80 (formed integral with the substrate 20) extends upward through the top plate 36 and a conductive trace 82 runs up the side of the post 80. The trace 82 begins at the innermost turn of the coil 42 and proceeds to a point where the trace 82 makes electrical contact with the upper cap layer 44. Preferably of monocrystalline silicon and highly doped to be conductive, the upper cap layer 44 serves as the electrical connection between the trace 82 and moveable electrode 64. If the upper cap layer 44 is not conductive, an additional conductive trace along the upper cap layer 44 to the moveable electrode 64 will be utilized. The outermost turn of the coil 42 is connected by an electrical trace 84. Where the upper cap layer 44 is conductive, a dielectric layer 86 insulates the trace 84 from the upper cap layer 44. Alternatively, a p-n junction structure (as further described below) could be used.

It is noted that the inner and outer turns of the coil 42 may be alternatively connected respectively to the fixed electrode 66 and the moveable electrode 64, thereby reversing the polarity of the LC tank circuit 22 if desired. Additionally, the particular paths between the coil 42 and the electrodes 66 and 64 may also be varied (e.g., such that both are included on the substrate 20) as best suited by the fabrication process. In all cases, the resistance of the electrical path through the traces 82, 84 and the upper cap layer 44 (if used) should be minimized.

The upper and lower cap layers 44 and 46 are bonded to the substrate 20 preferably via a hermetic sealing process. Alternatively, a post-bond coating of the entire sensing device 12 may be used to establish hermeticity. In either situation, steps are taken to minimize the residual gas pressure within the sensing device 12 after a hermetic seal is established. Once the initial hermetic seal is achieved, gas may be trapped in the interior of the sensing device 12 due to continued outgassing of the interior surfaces and/or the bonded regions. Gas pressure of the residual gas will increase within the interior chamber 90 of the pressure sensor 18 as the diaphragm 64 deflects during normal operation. This residual gas may effect the overall sensitivity of the pressure sensor 18 by effectively increasing the spring constant of the diaphragm 64. Additionally, the residual gas will expand and/or contract with changes in the temperature of the sensing device 12 itself, causing signal drift.

To compensate for the various negative effects of any residual gas, the pressure sensor 18 is provided with a displacement cavity 88. This displacement cavity 88 is generally seen in FIG. 3 and is in communication either directly or through a small connecting channel with the interior chamber 90 of the pressure sensor 18, defined between the diaphragm 64 and the fixed electrode 66. The displacement cavity 88 is sized such that the total internal sensor volume, the combined volume of the displacement cavity 88 and the interior chamber 90, varies minimally with deflection of the diaphragm 64 over its operational range of displacement. By minimizing the overall change in volume with deflection of the diaphragm 64, the effect of the residual gasses are minimized and substantially eliminated. In the preferred embodiment, the volume of the displacement cavity 88 is approximately ten times greater than the volume of the chamber 90. To further reduce temperature induced drift and to increase the sensitivity of the device 12, lower pressures within the internal volume 90 should be used.

In addition to the preferred embodiment, other configurations for the sensing device 12 are possible. Depending on the relative sizes of the diaphragm 64 and coil 42, the diaphragm 64 may be located within, above, or below the turns of the coil 42, as well as off to one end or side of the device 12 as seen in FIG. 3. The post 40 and/or one of the plates 36 or 38 of the magnetic core 33, may be omitted to simplify fabricating. However, this would be to the detriment of performance. Alternate lead transfer schemes may be used instead of the disclosed traces 82 and 84 that connect the coil 42 to the sensor 18. More or fewer wafer layers may be used to adapt manufacturing processing to available technologies. For example, the entire magnetic core 33 could be formed on the top side of the substrate 20, thereby eliminating the need for lower cap layer 46. Multiple coil layers could also be implemented to increase the coil turn count. Finally, the overall shape of the device 10 may be square, round, oval, or another shape.

Figure 9:
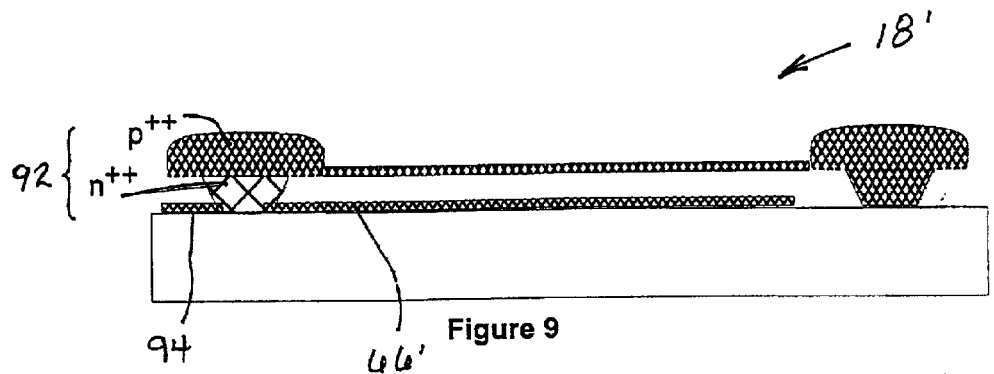
FIG. 9 is a diagrammatic illustration of one scheme for providing electrically isolated paths for the connections and electrodes of the capacitive sensor portion.
Figure 10:
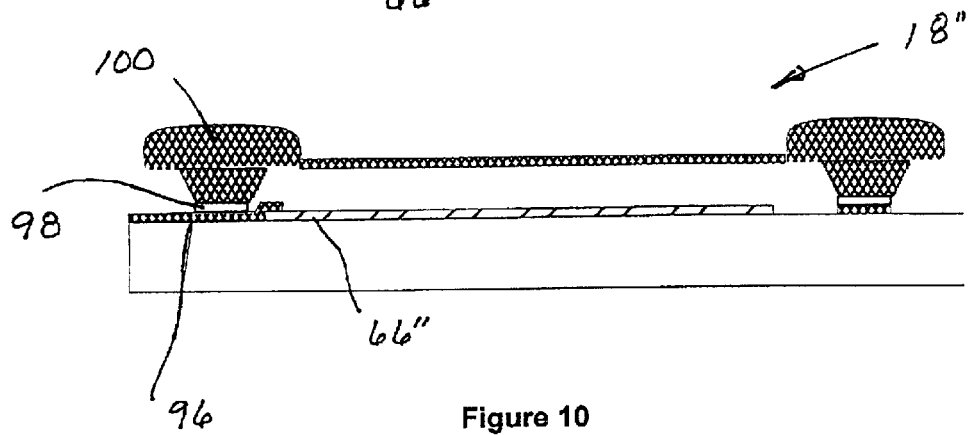
FIG. 10 is a diagrammatic illustration of another scheme for electrically isolating the conductive paths for the connections and contacts of the capacitive sensor portion.

To isolate the internal volume of the pressure sensor 18 from the internal volume of the integrated inductor 16, a hermetic lead transfer can be provided as a substitute for the dielectric layer 86. A hermetic lead transfer would eliminate outgassing from the inductor coil 42 and magnetic core 33 as a source of drift for the pressure sensor 18, thereby improving long-term stability. The hermetic lead transfer may be accomplished by any of several means that provide a sealed and electrically isolated conductive path. One example, of a mechanism for achieving a sealed and electrically isolated conductive path is through the use of a p-n junction structure 92 in the sensor 18'. This is illustrated in FIG. 9. The p-n junction structure 92 (with p-material forming the diaphragm) forms an electrically isolated path in a silicon layer and provides for electrical contact between a fixed electrode 66' and a lead trace 94 but not from the fixed electrode 66' to the diaphragm 66'.

In another alternative construction, a separate polysilicon layer 96 forms a conductive path to a fixed electrode 66". The conductive layer 96 is insulated, by a separate insulating layer 98, from the doped silicon rim 100 of the sensor 18".

An alternative embodiment of the present sensing device, designated as 12", includes active circuitry for immediate processing of the data including logging, error correction, encoding, analysis, multiplexing of multiple sensor inputs, etc. Since the sensing device 12" of this embodiment, seen in FIG. 11, includes numerous structures which are the same or identical to the structures seen in the embodiment illustrated in FIG. 3, like structures are accordingly provided with like designations and are not repetitively discussed. Reference should therefore be accordingly made to the preceding sections of this description where those structures are discussed in connection with FIG. 3.

Figure 11:
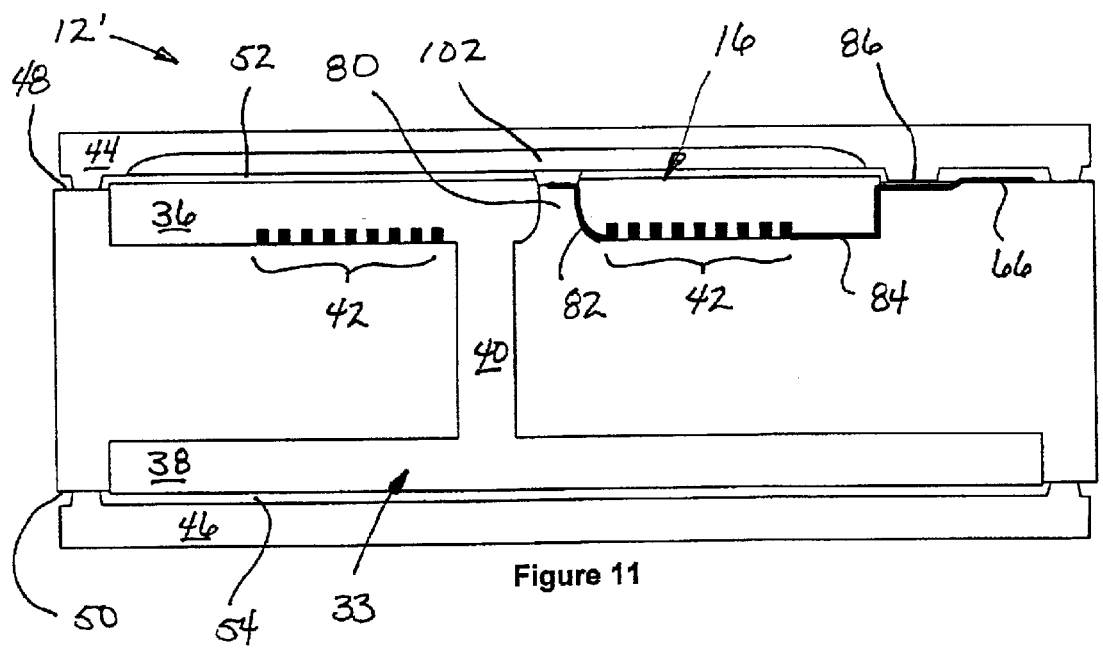
FIG. 11 is a cross-sectional view, generally similar to that seen in FIG. 3, further incorporating active circuitry into the sensing device.
Figure 12:
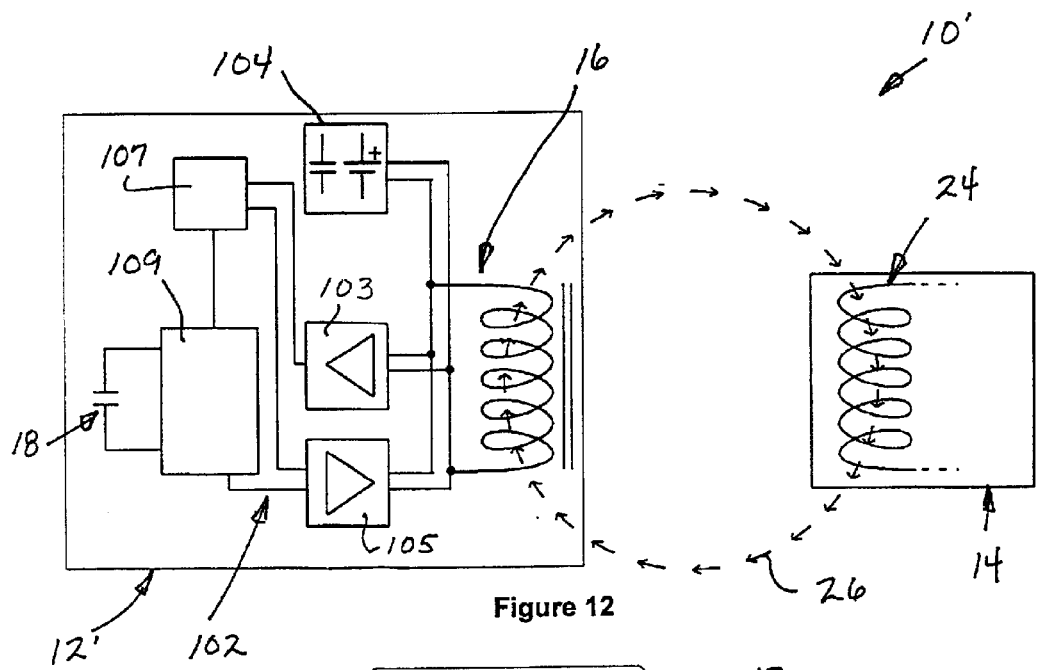
FIG. 12 is a block diagram illustrating one possible circuit implementation of the active circuitry when incorporated into the sensing device of the present wireless MEMS sensing system.
Figure 13:
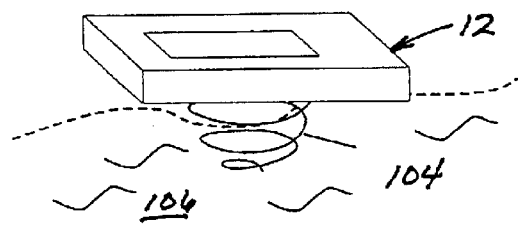
FIG. 13 illustrates one method of mounting, within the body of a patient, a sensing device embodying the principles of the presents invention.

The block diagram of FIG. 12 illustrates one possible circuit implementation for the active circuitry 102 seen in FIG. 11. In the illustrated configuration, the integrated inductor 16 serves as an antenna for RF telemetry with the external readout device 14. Using RF modulation schemes well know to those skilled in the art, the RF magnetic field 26 transmitted from the device 14 provides both data communication and necessary power to the circuitry 102. The received energy across inductor 16 is rectified and stored temporarily in an onboard capacitor or power supply designated at block 104. The input decoder 103 may receive digital data pertaining to short or long term memory or real time clock signals, and may transfer this information to the control logic 107. The front end conditioning circuitry 109 converts an analog sensor signal into a form that is encoded and amplified by the output driver 105. The integrated inductor 16 then serves to transmit the RF signal back to the external readout device 14, where the information can be processed, stored, or displayed. The many variations for circuit implementations of the rectifier of 104, modulation and coding schemes encompassing blocks 103 and 105, analog circuitry 109 and needed control logic 103 will be appreciated.

A key issue for sensing physiologic parameters in medical applications is that the sensor must be biocompatible. Biocompatibility involves two issues: the effect of the sensor on the body (toxicity), and the effect of the body on the sensor (corrosion rate). While the fabrication of the substrate 20 of Pyrex glass, as described in connection with FIG. 3, would be advantageous since Pyrex is highly corrosion resistant, additional measures must be taken to include the corrosion resistance of the silicon and other components of the sensing device 12. One method of improving those structures of the sensing device 12 formed of silicon, such as the upper and lower cap layers 44 and 46, is to fabricate those structures of heavily boron-doped silicon. Heavily boron-doped silicon is believed to be largely corrosion resistant and/or harmless to tissues in biologic environments.

Another method by which corrosion resistance of the implanted device 12 may be improved is through coating of the device 12 with titanium, iridium, Parylene (a biocompatible polymer), or various other common and/or proprietary thick and thin films. Such a coated device provides two levels of corrosion resistance: and underlying stable surface and a separate, stable coating (which may also be selectively bioactive or bioinert). Provided with these two levels of corrosion resistance, even if the outer coating contains pinholes, cracks, or other discontinuities, the device 12 retains a level of protection.

A number of different, and at times application-specific, schemes can be envisioned for long-term use of the sensing device 12 of the present invention. In general, it is necessary to anchor the device 12 so that migration of the device 12 does not occur within the patient. A dislodged device 12 may migrate away from the physiologic parameter intended to be sensed, thereby rendering the device 12 useless for its intended purpose and requiring implantation of another device 12. A variety of such anchoring schemes is discussed below.

Figure 14:
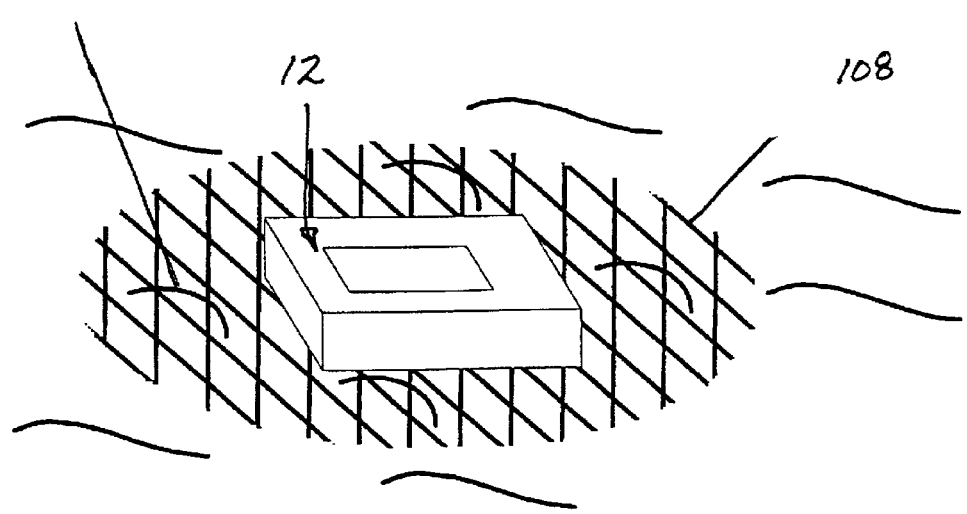
FIG. 14 illustrates a second embodiment by which a sensing device embodying the principles of the present invention may be secured to tissues within the body of a patient

Referring now to FIG. 14, a screw (or stud) 104 is attached to the lower cap layer 46 of the sensing device 12. Preferably, the screw 104 is attached to the lower cap layer 46 with biocompatible epoxy or a similar method. The screw 104 is then embedded into tissue 106 of the patient and the device 12 retained in place. Preferred materials for the screw 104 include stainless steel and titanium.

Another scheme for securing the sensing device 12 within a patient is seen in FIG. 14. As seen therein, the sensing device 12 has secured to the lower cap layer 46 a sheet of mesh 108. The mesh 108 becomes encapsulated by tissue of the patient over time, thus anchoring the sensing device 12. Sutures 110 may be used to hold the sensing device 12 in place until encapsulation occurs. Preferred materials for the mesh 108 include loosely woven, biocompatible cloth and the mesh 108 may range in size from 1 to 20 mm.

Figures 15, 16, 17:
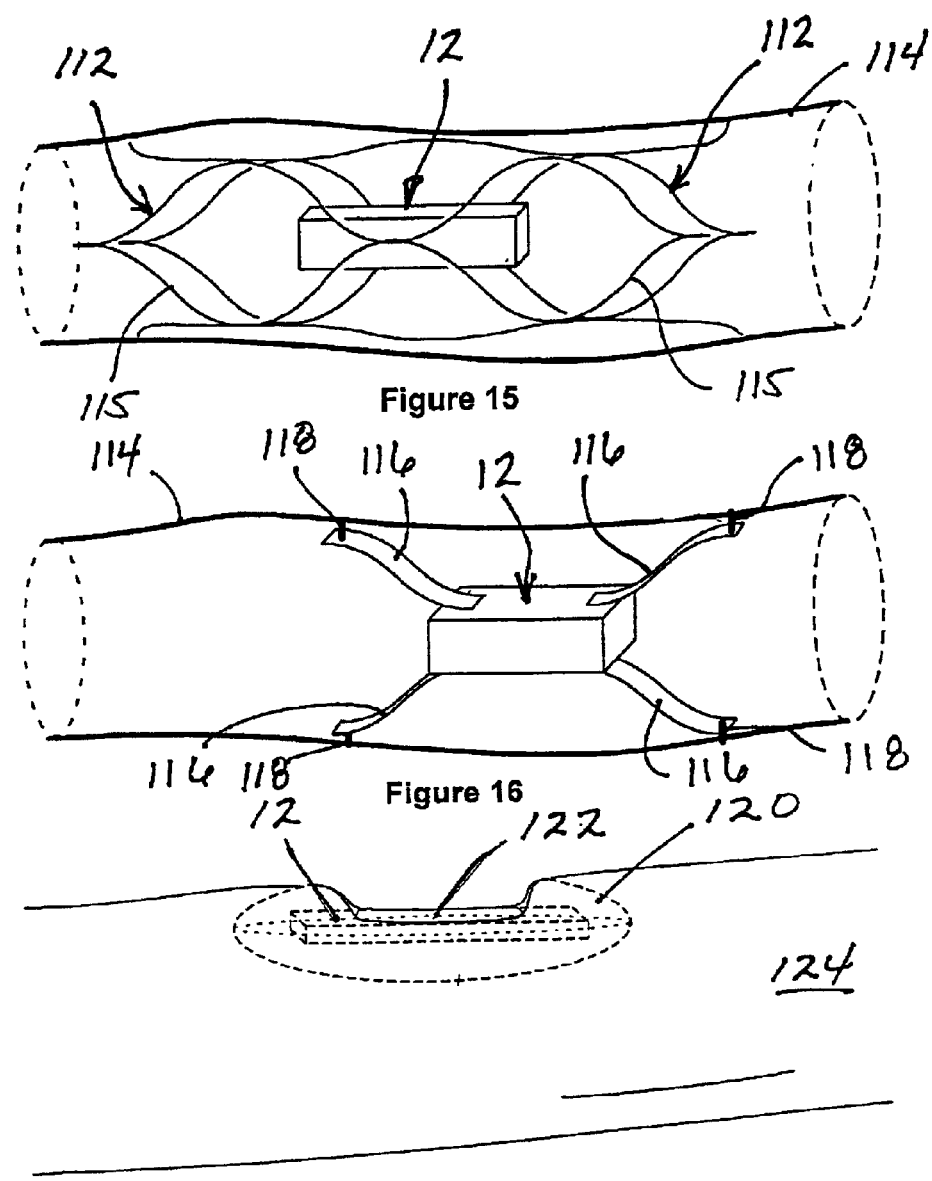
FIGS. 15 and 16 are diagrammatic illustrations of different embodiments for locating a sensing device according to the principles of the present invention, within a vessel in the body of a patient.
FIG. 17 illustrates a sensing device, according to the principles of the present invention, encapsulated in a material yielding a pellet-like profile for implantation into the tissues in the body of a patient.

An endoluminal attachment scheme is illustrated within FIG. 15. In this application, sensing device 12 is attached to stent-like spring cage 112. As such, the sensing device 12 may be non-surgically injected into a blood vessel 114 or other body cavity containing fluid flow. After ejection from the insertion apparatus (not shown), the spring cage 112 expands and lodges the sensing device 12 at the sensing location, while allowing blood (or other fluid) to continue flowing past the sensing device 12. To expand outward, the spring cage 12 is formed so that the arms 115 thereof are resiliently biased outward. Preferred materials for the arms 115 include stainless steel or titanium. The arms 115 may also be in wire or other forms.

Another endoluminal attachment scheme is shown in FIG. 16. In this embodiment, the sensing device 12 is anchored in place within vessel 114 by a set of radially outwardly expandable spring arms 116. The spring arms 116 may be provided with depth-limited anchoring tips 118 on their ends to further secure the sensing device 12. The arms 116 may be in wire, ribbon or other form and are biased outwardly to cause engagement of the anchoring tips 118 with the wall of the vessel 114. Preferred materials for the arms 116 and for the anchoring tips 118 include stainless steel or titanium.

In FIG. 17, the sensing device 12 is encapsulated in a biocompatible material such as poly(methyl methacrylate), yielding a pellet-like profile designated at 120. A recess 122 formed in the pellet 120 allows access to the movable element 64. In addition to providing an alternate form factor that may be less mechanically irritating to tissue 124 both during and after implantation, such an embodiment may better allow the sensing device 12 to be incorporated into the body of a medical device, such as an extrusion, injection-molded part, soft rubber, or other material, that otherwise would poorly anchor to a rectangular or other geometrically shaped sensing device 12. Obviously, encapsulation could be used to give the sensing device other profiles or form factors as well.

From the above, it can be seen that many applications exist for the system 10 of the present invention. Some illustrative examples of such applications are described hereafter.

Figure 18:
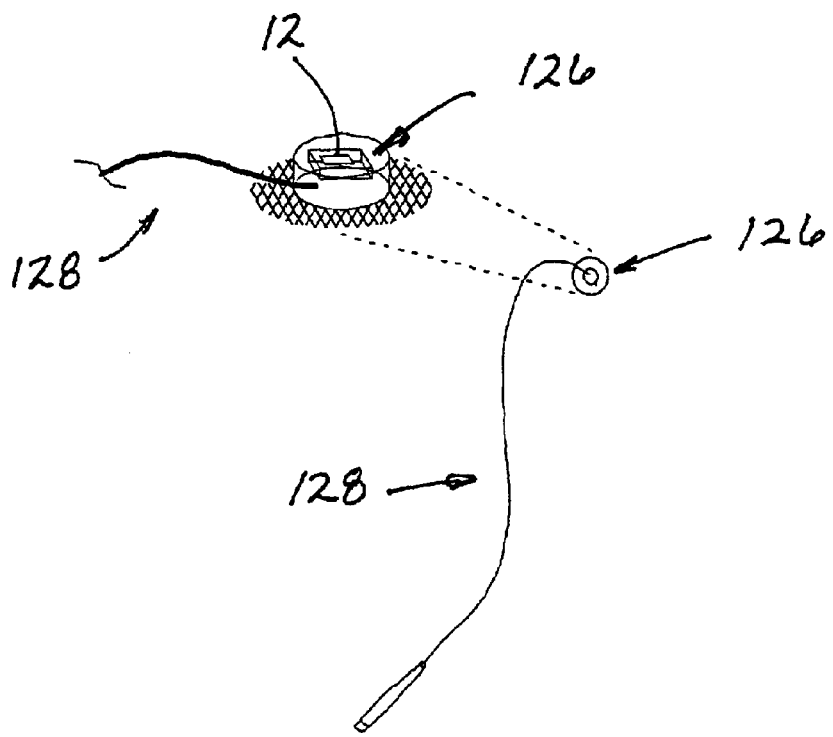
FIG. 18 illustrates a sensing device according to the principles of the present invention being located within the electrode tip of an implantable stimulation lead, such as that used for cardiac pacing.

One application of the described technology, depicted in FIG. 18, locates the sensing device 12 in an electrode tip 126 of an implantable stimulation lead 128, such as a stimulation lead used for cardiac pacing. In such an arrangement, the sensing device 12 could be used with the read-out device 14 for monitoring arterial, atrial, ventricular, and/or other blood pressures.

Figure 19:
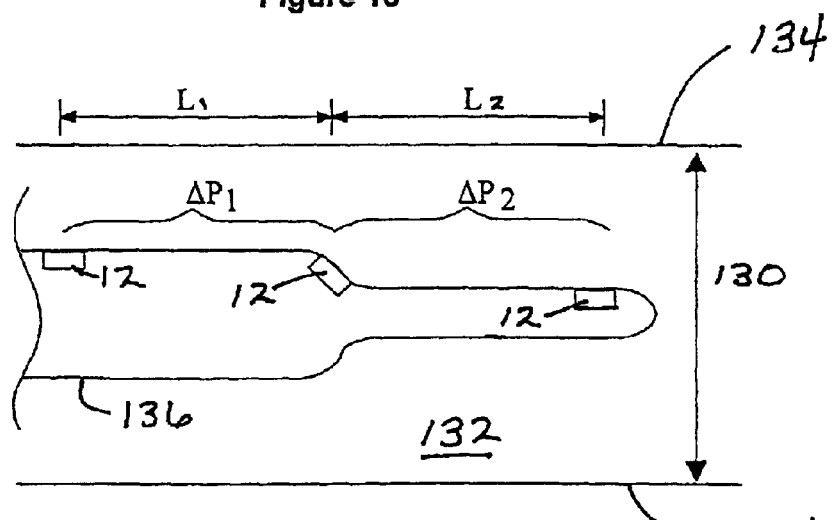
FIG. 19 illustrates a plurality of sensing devices according to the present invention located within a catheter and utilized to calculate various physiologic parameters within a vessel within the body of a patient.

In the application seen in FIG. 19, three sensing devices 12 are being used to calculate a diameter 130 of a flow path 132 defined by walls 134. In addition to the diameter 130, mass and/or volumetric blood or other fluid flow rates through the flow path 132 may be calculated. The sensing devices 12 are located in a variable diameter catheter 136 or similar geometric construction conductive to taking such measurements. Computational fluid dynamics (CFD) models and calculations utilizing the distances between the sensing devices 12 ($L_1$ and $L_2$) and pressure changes $\Delta P_1$ and $\Delta P_2$ therebetween, can be used to derive the desired parameters from suitably precise pressure data.

Figure 20:
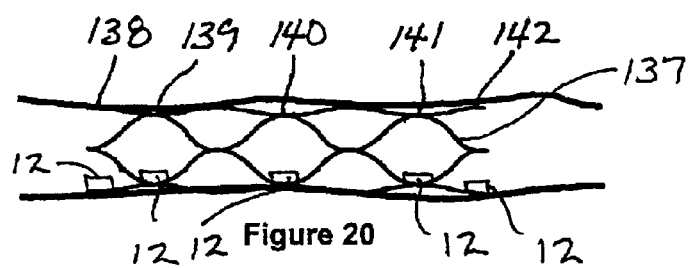
FIG. 20 is a schematic illustration of multiple sensors being used to measure performance of a component in the body or a device mounted within the body of a patient.

Cardiac monitoring applications can particularly benefit from the present system 10 in its various embodiments. One possibility is to locate the sensing devices 12 (either by means of a multiple-sensor catheter or individually placed sensor devices 12 (or placed as a tethered pair)) at appropriate locations around a natural or artificial heart valve or other biologic valve, to monitor the pressure on either side of, and/or the flow through, the valve. The same setup may also be used to monitor pressure along a vascular stent 137, as shown in FIG. 20. Sensing devices 12 may be placed at one or more locations 138–142 along the length of the stent.

Figure 21:
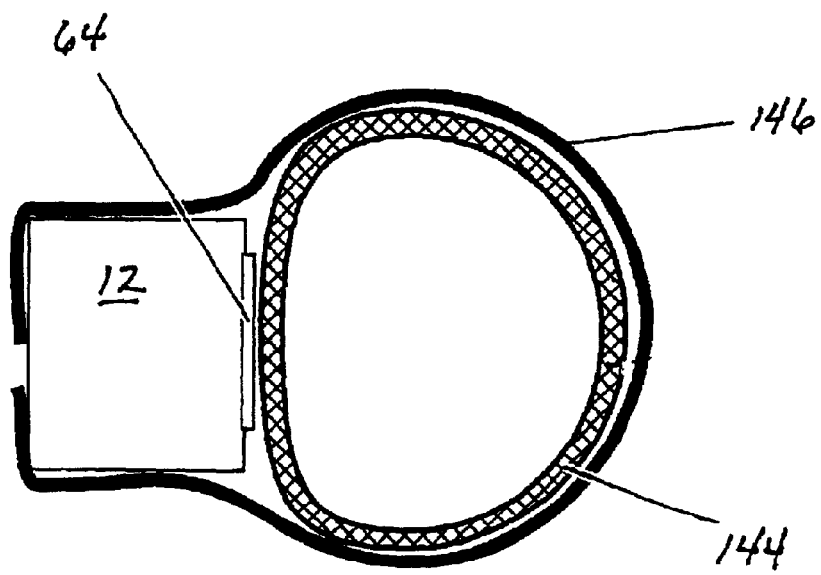
FIG. 21 illustrates a sensing device according to the principles of the present invention being utilized to measure pressure externally through a vessel wall.

Referring now to FIG. 21, a sensing device 12 is located such that pressure is measured externally through a vessel wall 144, such as the wall of a blood vessel. The sensing device 12 is placed in intimate contact with the wall 144 through use of a variety of means, including adhesive clips 146 (of a biocompatible material), tissue growth or other methods. The sensing device 12 is oriented so that the moveable element 64 is adjacent the vessel wall 144 and measures pressure transduced through the vessel wall 144. A calibration factor in active circuitry may be used to adjust the measured value to an actual value so as to account for the effects of sensing the pressure through the vessel wall 144.

Figure 22:
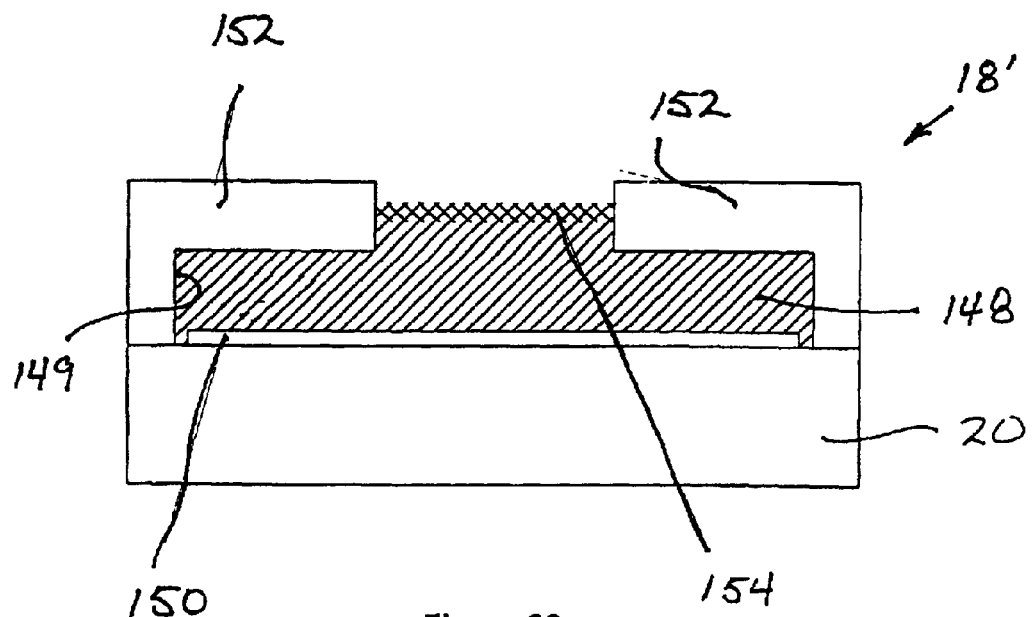
FIG. 22 illustrates a portion of a further embodiment of the present invention in which the pressure sensing features of the sensing device have been augmented over or replaced with a structure allowing a parameter other than pressure to be sensed.

As an alternative to the foregoing embodiments, the pressure sensor 18 of the sensing device 12 may be augmented and/or replaced with a structure or sensor 18' that allows a parameter other than pressure to be sensed. For clarity, in FIG. 22 only the sensor 18' portion of the sensing device 12 is shown, the nonillustrated elements being as previously discussed. In the sensor 18', a chemical-sensitive substance 148 is placed in a confinement cavity 149 and contact with and exterior surface of sensor diaphragm 150. Osmotic expansion of the substance 148, in response to the concentration of a target chemical, generates a pressure on the diaphragm 150 and allowing the concentration of the chemical to be monitored. For convenience, only the substrate 20 is illustrated, the fixed electrode and associated structures be omitted. This sensor 18' may optionally include cap structure 152 to restrict the expansion of the chemical sensitive substance 148 to the center of the diaphragm 150 to maximize deflection of the diaphragm 150. A micromachined mesh, grid, or semipermeable membrane 154, also optional and either integral to the cap or attached separately thereto, may be included to prevent the chemical sensitive substance 148 from escaping (or bulging out of) the confinement cavity 149, and/or to prevent foreign materials from entering the cavity 149. The mesh 154 could also exist on the molecular level, being formed of a material such as a cross-linked polymer.

In another alternative parameter sensing embodiment, a material with high thermal coefficient of expansion is placed between moveable and fixed electrodes in a structure otherwise constructed similar to a capacitive sensor structure, thereby forming a temperature sensor.

Figure 23:
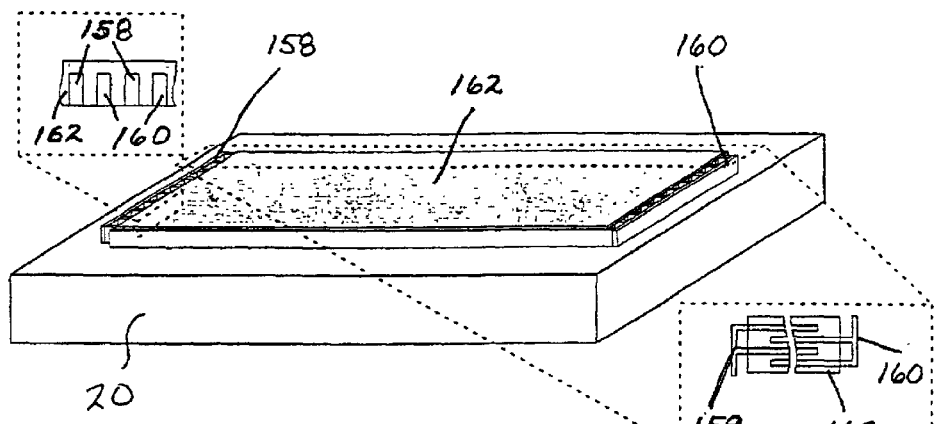
FIG. 23 is schematic perspective view, with portions enlarged, illustrating an alternative embodiment for sensing according to the principles of the present invention.
Figure 24:
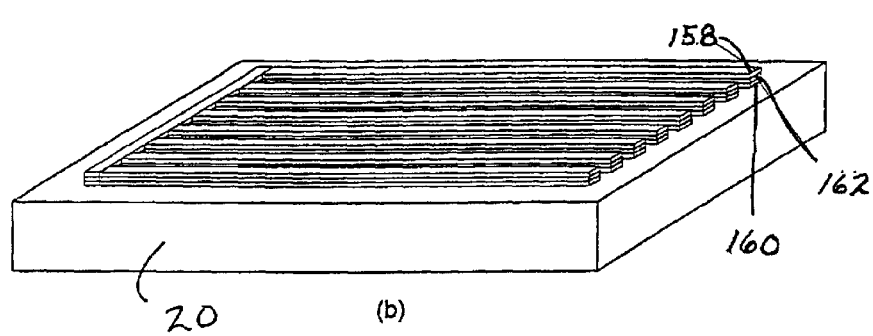
FIG. 24 is an embodiment generally similar to that seen in FIG. 23 for sensing according to the principles of the present invention.

FIG. 23 illustrates an alternative capacitive sensor 156 on the substrate 20, additional structures are omitted for clarity. In this sensor 156, the capacitance changes due to a varying dielectric constant within the capacitive gap defined between electrodes 158 and 160. The gap is filled with sensing substance 162 chosen such that its dielectric constant changes in response to the particular physiologic stimulus being evaluated. FIG. 24 depicts an alternate implementation of the above embodiment, with the electrodes 158' and 160' and the sensing substance 162 being stacked vertically on the substrate 20, as opposed to the lateral orientation in FIG. 23.

The pressure, temperature or other data sensing technology, in its various forms, may be incorporated into an open or closed-loop therapeutic system for the treatment of medical conditions which require or benefit from regular, subcutaneous monitoring of pressures or other parameters. The system may be used, for example, to control the administration of drugs. One particular application of this would be to control hyper- or hypotension. In the preferred embodiment, pressure data from the sensor, alone or in conjunction with other real-time or preexisting data, is used to adjust drug or other therapy for hypo- or hypertensive patient. Therapy is provided by means of a control module worn by, or implanted within, the patient (similar to e.g., an insulin pump for diabetics). The module may alert the user to take action, directly administer a drug intravenously, and/or initiate other invasive or non-invasive responses. Furthermore, relevant information (including, but not limited to, measure physiologic parameters, treatment regimens, data histories, drug reservoir levels) can further be transmitted from the control module to other locations via cellular phone, wireless infrared communication protocols or other communication methods and mechanisms.

Other applications of the implantable wireless sensing device of this invention include, without limitation, the following: 1) Monitoring congestive heart failure patients such as left ventricle pressure monitoring, left atrium pressure monitoring and pulmonary artery pressure monitoring; 2) other hemodynamics parameters including blood pressure, blood flow velocity, blood flow volume and blood temperature; 3) diabetic applications including glucose level monitoring; 4) urinary applications such as bladder pressure and urinary tract pressure measuring; and 5) other blood parameters including $O_2$ saturation, pH, $CO_2$ saturation, temperature, bicarbonate, glucose, creatine, hematocirt, potassium, sodium, chloride; and 6) cardiac parameters including (previously discussed) valve pressure gradients and stent pressure gradients.

In addition to single sensor, an array of different sensors may be fabricated or assembled on one sensing device to enhance artifact removal and/or selectivity/differentiation between signals. A discussion of such a construction best details this construction. Local pressure or pH variations can add spurious signals to a pressure- or pH-based glucose sensor. To compensate for these spurious signals, adjacent pH or pressure reference sensors may be implemented to measure these environmental parameters. External sensors may also be used to compensate for factors such as atmospheric pressure. A combination of sensor arrays, fuzzy logic, look-up tables, and/or other signal-processing technologies could all be used to effect such compensation.

The foregoing disclosure is the best mode devised by the inventor for practicing the invention. It is apparent, however, that several variations in accordance with the present invention may be conceivable to one of ordinary skill in the relevant art. Inasmuch as the foregoing disclosure is intended to enable such person to practice the instant invention, it should not be construed to be limited thereby, but should be construed to include such aforementioned variations, and should be limited only by the spirit and scope of the following claims.

What is claimed is:

1. An implantable microfabricated sensor device for measuring a physiologic parameter of interest within a patient, said sensor comprising:

an implantable sensing device, said sensing device being a micro electromechanical system (MEMS) comprising a substrate, an integrated inductor formed on the substrate, at least one sensor responsive to the physiologic parameters and being formed at least in part on the substrate, a plurality of conductive paths electrically connecting said integrated inductor with said sensor, said integrated inductor, said sensor and said conductive paths cooperatively defining an LC tank resonator.

2. The sensor device of claim 1 wherein said sensor is a capacitive sensor having a fixed electrode and a moveable electrode.

3. The sensor device of claim 2 wherein said fixed electrode is formed on said substrate.

4. The sensor device of claim 2 wherein said sensor is a pressure sensor.

5. The sensor device of claim 2 wherein said sensor is a temperature sensor.

6. The sensor device of claim 2 wherein said sensor is a chemical sensor.

7. The sensor device of claim 1 wherein said integrated inductor includes a magnetic core and a winding comprised of a conductive material about said magnetic core.

8. The sensor device of claim 7 wherein said magnetic core includes a plate member formed on a first face of said substrate.

9. The sensor device of claim 8 wherein said magnetic core further includes a second plate member, said second plate member being formed on a second face of said substrate and located generally opposite of said first plate member.

10. The sensor device of claim 9 further comprising a post extending through said substrate and connecting said first plate to said second plate.

11. The sensor device of claim 8 wherein said winding is formed within said first plate.

12. The sensor device of claim 8 further comprising a cap layer formed over said plate member.

13. The sensor device of claim 12 wherein said cap layer includes a portion defining a moveable electrode of said sensor.

14. The sensor device of claim 12 wherein said cap layer is conductive.

15. The sensor device of claim 12 wherein said cap layer is doped silicon.

16. The sensor device of claim 7 wherein said magnetic core includes first and second plate members connected to one another by post.

17. The sensor device of claim 16 wherein said windings are about said post.

18. The sensor device of claim 17 wherein said windings are about said post and adjacent to said first plate.

19. The sensor device of claim 1 further comprising active circuitry being formed in said sensing device.

20. The sensor device of claim 19 wherein said active circuitry is formed within a cap layer formed over said integrated inductor.

21. The sensor device of claim 1 wherein said sensor device is wireless.

22. The sensor device of claim 1 wherein said sensing device is monolithic.

23. The sensor device of claim 1 further comprising at least two sensors.

24. The sensor device of claim 23 wherein said two sensors sense the same physiologic parameter.

25. The sensor device of claim 23 wherein said two sensors sense different physiologic parameters.

26. The sensor device of claim 1 wherein said sensor is a capacitive sensor including a fixed electrode and a moveable electrode, said fixed and moveable electrodes defining a chamber therebetween, said chamber being in fluid communication with a displacement cavity.

27. The sensor device of claim 26 wherein said displacement cavity is defined within said substrate.

28. The sensor device of claim 1 wherein said sensor is a capacitive sensor having a fixed electrode and a moveable electrode, said fixed and moveable electrodes being electrically coupled by first and second traces to said integrated inductor, said first and second traces being electrically isolated from one another.

29. The sensor device of claim 28 wherein said traces are isolated by a dielectric layer therebetween.

30. The sensor device of claim 28 wherein said traces are isolated by a p-n junction structure.

31. The sensor device of claim 1 as part of a sensing system further comprising a non-implantable readout device, said readout device including a second inductor adapted to magnetically couple with said integrated inductor to read changes in said LC tank resonator as a result of said sensor sensing the physiologic parameter of interest.

* * * * *

(12) INTER PARTES REVIEW CERTIFICATE (2081st)
United States Patent
Rich et al.

(10) Number: US 6,926,670 K1
(45) Certificate Issued: May 14, 2021

(54) WIRELESS MEMS CAPACITIVE SENSOR FOR PHYSIOLOGIC PARAMETER MEASUREMENT

(75) Inventors: Collin A. Rich; Matthew Z. Straayer; Yafan Zhang; Nader Najafi; Sonbol Massoud-Ansari

(73) Assignee: INTEGRATED SENSING SYSTEMS, INC.

Trial Numbers:

IPR2019-01338 filed Jul. 15, 2019
IPR2019-01339 filed Jul. 15, 2019

Inter Partes Review Certificate for:

Patent No.: 6,926,670
Issued: Aug. 9, 2005
Appl. No.: 10/054,330
Filed: Jan. 22, 2002

The results of IPR2019-01338 and IPR2019-01339 are reflected in this inter partes review certificate under 35 U.S.C. 318(b).

INTER PARTES REVIEW CERTIFICATE
U.S. Patent 6,926,670 K1
Trial No. IPR2019-01338
Certificate Issued May 14, 2021

AS A RESULT OF THE INTER PARTES REVIEW PROCEEDING, IT HAS BEEN DETERMINED THAT:

Claims 1-5, 21-29 and 31 are cancelled.

\* \* \* \* \*